(12) United States Patent
Toyoshiba (10) Patent No.: US 12,026,461 B1
(45) Date of Patent: Jul. 2, 2024

(54) DATA ANALYSIS APPARATUS AND DATA ANALYSIS PROGRAM

(71) Applicant: FRONTEO, Inc., Tokyo (JP)

(72) Inventor: Hiroyoshi Toyoshiba, Tokyo (JP)

(73) Assignee: FRONTEO, Inc., Tokyo (JP)

( * ) Notice: Subject to any disclaimer, the term of this patent is extended or adjusted under 35 U.S.C. 154(b) by 0 days.

(21) Appl. No.: 18/554,324

(22) PCT Filed: Dec. 20, 2022

(86) PCT No.: PCT/JP2022/046938
§ 371 (c)(1),
(2) Date: Oct. 6, 2023

(51) Int. Cl.
*G06F 17/10* (2006.01)
*G06F 17/16* (2006.01)
*G06F 40/20* (2020.01)
*G06F 40/247* (2020.01)
*G06F 40/284* (2020.01)
*G16C 20/90* (2019.01)

(52) U.S. Cl.
CPC .............. *G06F 40/20* (2020.01); *G06F 17/16* (2013.01); *G16C 20/90* (2019.02)

(58) Field of Classification Search
USPC ............ 382/154–308; 704/1–275; 706/1–62, 706/900–903; 707/706–812
See application file for complete search history.

(56) References Cited

U.S. PATENT DOCUMENTS

| | | | | |
|---|---|---|---|---|
| 5,555,320 A * | 9/1996 | Irie | .................... | G06F 18/213 382/157 |
| 6,408,321 B1 * | 6/2002 | Platt | ................... | G06F 18/2132 702/22 |
| 11,704,552 B2 * | 7/2023 | Sim | .................... | G06N 3/08 706/25 |
| 2010/0179933 A1 | 7/2010 | Bai et al. | | |
| 2011/0052050 A1 * | 3/2011 | Cao | ................... | G06V 10/50 382/165 |
| 2020/0019877 A1 | 1/2020 | Okanohara et al. | | |
| 2020/0152295 A1 * | 5/2020 | Gibson | ................ | G16C 20/62 |

(Continued)

FOREIGN PATENT DOCUMENTS

JP 3163185 B2 5/2001
JP 2011022912 A 2/2011
(Continued)

OTHER PUBLICATIONS

Supplementary European Search Report issued on Mar. 27, 2024 for corresponding European Application No. 22 93 6714.

*Primary Examiner* — Marcellus J Augustin (74) *Attorney, Agent, or Firm* — POLSINELLI PC (57) ABSTRACT

Vector computation units 1 and 2 for forming first and second vector spaces by computing a plurality of feature vectors from each of a first data set and a second data set, and a vector mapping unit 3 for mapping a feature vector not synonymous with a feature vector in the second vector space from the first vector space to the second vector space are included. Further, by mapping a feature vector not synonymous with a plurality of feature vectors included in the second vector space from the first vector space to the second vector space without changing the plurality of feature vectors, data analysis can be performed on, as targets, a feature vector originally included in the second vector space and a feature vector added from the first vector space.

12 Claims, 4 Drawing Sheets

(56) References Cited

U.S. PATENT DOCUMENTS

| | | | |
|---|---|---|---|
| 2020/0192973 A1* | 6/2020 | Raghunathan | G06F 40/157 |
| 2020/0226126 A1* | 7/2020 | Zou | G06N 3/084 |
| 2023/0082663 A1* | 3/2023 | Joshi | G06F 40/247 |
| | | | 704/9 |
| 2023/0084638 A1* | 3/2023 | Yang | G16B 15/00 |
| | | | 706/12 |
| 2023/0169371 A1* | 6/2023 | Kulshreshtha | G06N 5/048 |
| | | | 707/694 |
| 2023/0289374 A1* | 9/2023 | Toyoshiba | G06F 16/338 |
| 2023/0385541 A1* | 11/2023 | Ben Shahar | G06F 40/20 |

FOREIGN PATENT DOCUMENTS

| | | |
|---|---|---|
| JP | 5364996 B2 | 12/2013 |
| JP | 2020098646 A | 6/2020 |
| JP | 6976537 B1 | 12/2021 |

* cited by examiner

$$DW = \begin{pmatrix} w_1 & w_2 & \cdots & w_n \\ \begin{pmatrix} dw_{11} \\ dw_{21} \\ \vdots \\ dw_{m1} \end{pmatrix} & \begin{pmatrix} dw_{12} \\ dw_{22} \\ \vdots \\ dw_{m2} \end{pmatrix} & \cdots & \begin{pmatrix} dw_{1n} \\ dw_{2n} \\ \vdots \\ dw_{mn} \end{pmatrix} \end{pmatrix}$$

FIG. 5

(a) FIRST VECTOR SPACE  (b) SECOND VECTOR SPACE

$$CF = \begin{pmatrix} cf_{11} & cf_{12} & \cdots & cf_{1j} \\ cf_{21} & cf_{22} & \cdots & cf_{2j} \\ \vdots & \vdots & \ddots & \vdots \\ cf_{i1} & cf_{i2} & \cdots & cf_{ij} \end{pmatrix} \begin{matrix} c_1 \\ c_2 \\ \vdots \\ c_i \end{matrix}$$

DATA ANALYSIS APPARATUS AND DATA ANALYSIS PROGRAM

CROSS REFERENCE TO RELATED APPLICATIONS

This application is a National Phase filing under 35 U.S.C. § 371 of PCT/JP2022/046938, filed on Dec. 20, 2022; the entire contents of which application is herein incorporated by reference.

TECHNICAL FIELD

The present invention relates to a data analysis apparatus and data analysis program, and is particularly suitable for data analysis using a vector operation.

BACKGROUND ART

Conventionally, data analysis using a vector operation has been utilized in a lot of industrial fields such as a pattern recognition system, an information search system, a prediction processing system, and a motion control system. In this type of data analysis, the feature amounts of individual data are represented by vectors, and processing such as pattern recognition and information search is executed based on the vectors. For example, a technology has been known in which individual target data is plotted on a two-dimensional (2D) plane based on feature vectors generated from the individual target data, and data analysis is performed using a 2D map generated in this way (for example, see PTL 1).

In an information search apparatus described in PTL 1, a 2D map in which a plurality of search targets (for example, texts) is plotted on a 2D plane is generated based on coordinate information on the basis of a plurality of feature vectors characterizing the plurality of search targets, respectively, and the 2D map is displayed on a screen. In addition, a feature vector that characterizes a search target (text) or a related element (a word included in the text) input as any search key information is specified, and a predetermined reference mark is displayed at a corresponding position on the 2D map based on coordinate information on the basis of the specified feature vector. Then, a search target corresponding to a plot included in a region specified by a user operation on the 2D map displayed on the screen together with the reference mark is extracted.

As in the technology described in PTL 1, when a feature vector is computed from a plurality of pieces of data contained in a certain data set, the computed feature vector has a configuration that depends on the size and content of the data set. For example, when a data set including a plurality of texts is targeted, and a relative feature of a word contained in each text within the data set is computed as a word vector, the word vector has a configuration that depends on the data set.

Here, when a word vector is computed for a word in a text included in a first data set, and a word vector is computed for a word in a text included in a second data set, even if the words are the same, the word vector computed from the first data set and the word vector computed from the second data set have different configurations. A reason therefor is that a word usage in each text included in the first data set and a word usage in each text included in the second data set have different tendencies, and the different tendencies are reflected in the configurations of the word vectors.

Therefore, a vector space formed by a plurality of feature vectors computed from a certain data set reflects features of the data set. In the technology described in PTL 1, the vector space thus formed is represented in the form of a 2D map, and data analysis is performed on the 2D map.

A technology has been known in which a feature vector computed from input data is mapped from a vector space to which the feature vector belongs to another vector space to generate a new feature vector, and data analysis is performed using the new feature vector (for example, PTLs 2 and 3). In addition, there has been a known method of a vector operation that can suppress deterioration in calculation accuracy of principal component analysis while reducing the amount of calculation (for example, see PTL 4).

In a similar user discovery system described in PTL 2, a representative group representing a predetermined group is extracted based on information indicating a link relationship between groups, and by approximating a group using the representative group, an element of a first vector space based on the group (corresponding to an individual user belonging to the group) is mapped to a second vector space based on the representative group. Then, a degree of similarity between users is computed based on the mapped element of the second vector space.

In a recognition apparatus described in PTL 3, for a subset that approximates a distribution in a vector space formed by a feature vector extracted from input pattern data, nonlinear transformation is performed in which each point in the set is mapped to a predetermined linear space, data after this nonlinear transformation is compared with standard data registered in advance in a dictionary means, and a comparison result thereof is output as a result of pattern recognition.

In an analysis apparatus described in PTL 4, by solving an eigenvalue problem using n d-dimensional vectors $x=\{x_1, x_2, \ldots, x_n\}$ given as a sample and m (m<n) d-dimensional vectors $y=\{y_1, y_2, \ldots, y_m\}$ acquired separately therefrom, r eigenvectors $z=\{z_1, z_2, \ldots, z_r\}$ representing features of the d-dimensional vectors x are computed. Then, the d-dimensional vectors x are converted into r-dimensional vectors y using the r eigenvectors z. In this way, it is possible to reduce the amount of calculation when compared to a kernel principal component analysis method using n d-dimensional vectors x, and it is possible to calculate a feature vector y with higher accuracy when compared to the case where kernel principal component analysis is performed using only m d-dimensional vectors y.

CITATION LIST

Patent Literature

PTL 1: JP6976537B
PTL 2: JP5364996B
PTL 3: JP3163185B
PTL 4: JP2011-22912A

SUMMARY OF INVENTION

Technical Problem

When data analysis is performed by computing a feature vector from a plurality of pieces of data included in a certain data set as in the technology described in PTL 1, data analysis cannot be performed beyond a vector space to which the feature vector belongs. For example, when data analysis is performed on a target paper in a certain technical field, data analysis cannot be performed beyond a range of texts described in the target paper. Therefore, data analysis can only be performed on known findings written in the paper in the technical field.

On the other hand, for example, when the first data set and the second data set are combined to create a larger data set, and data analysis is performed on the large data set as a target, coverage of data analysis is broadened to some extent. However, as a result, a feature of a vector space when a feature vector is computed for only the first data set as a target and a feature of a vector space when a feature vector is computed for only the second data set as a target are diluted, which causes a problem in that it becomes difficult to perform data analysis that fully utilizes the features of the vector spaces before combination.

The invention has been made to solve such a problem, and an object of the invention is to enable data analysis with coverage extended to a data set in a wider range while fully utilizing a feature of a vector space formed from an original data set.

Solution to Problem

To solve the above-mentioned problem, in the invention, a first vector space is formed by computing a plurality of feature vectors from a plurality of pieces of data included in a first data set, and a second vector space is formed by computing a plurality of feature vectors from a plurality of pieces of data included in a second data set. In addition, a feature vector included in the first vector space, which is a feature vector of an item not synonymous with a feature vector included in the second vector space, is mapped from the first vector space to the second vector space according to a mapping vector. Then, data analysis is performed on, as targets, a plurality of feature vectors computed in the second vector space and a feature vector mapped from the first vector space to the second vector space in the second vector space.

Advantageous Effects of Invention

According to the invention configured as described above, a first vector space and a second vector space are formed by individually computing a plurality of feature vectors from each of a plurality of pieces of data included in a first data set and a plurality of pieces of data included in a second data set, and thus the first vector space and the second vector space utilize the features of the first data set and the second data set, respectively, without change. In addition, while leaving the plurality of feature vectors included in the second vector space without change, by mapping feature vectors of items not synonymous with the feature vectors from the first vector space to the second vector space, feature vectors derived from the first vector space are added to the second vector space. Then, data analysis is performed on the feature vectors originally included in the second vector space and the feature vectors added by mapping from the first vector space as targets. In this way, according to the invention, it is possible to perform data analysis extending coverage to a data set wider than the second data set while fully utilizing the features of the original second vector space formed from the second data set.

DESCRIPTION OF EMBODIMENTS

Figure 1:
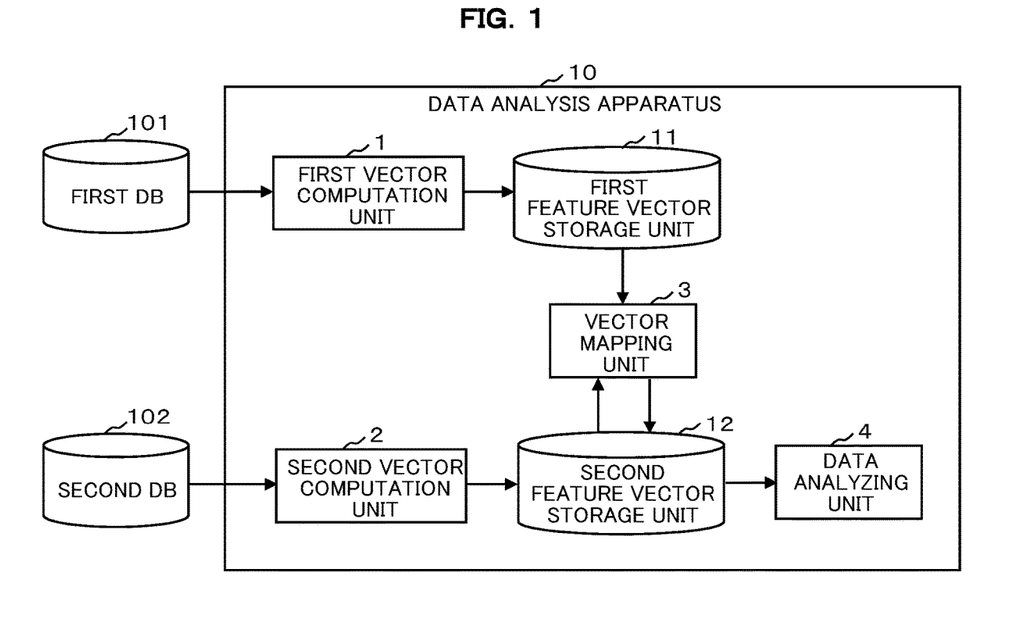
FIG. 1 is a block diagram illustrating a functional configuration example of a data analysis apparatus according to an embodiment.

An embodiment of the invention will be described below with reference to the drawings. FIG. 1 is a block diagram illustrating a functional configuration example of a data analysis apparatus 10 according to the present embodiment. As illustrated in FIG. 1, the data analysis apparatus 10 of the present embodiment includes a first vector computation unit 1, a second vector computation unit 2, a vector mapping unit 3, and a data analyzing unit 4 as functional configurations. Further, the data analysis apparatus 10 of the present embodiment includes a first feature vector storage unit 11 and a second feature vector storage unit 12 as storage media.

The functional blocks 1 to 4 can be configured by any one of hardware, DSP (Digital Signal Processor), and software. For example, when configured by software, the functional blocks 1 to 4 includes a CPU, a RAM, a ROM, etc. of a computer, and is realized by operating a program stored in a storage medium such as the RAM, the ROM, a hard disk, or semiconductor memory.

The data analysis apparatus 10 of the present embodiment performs data analysis using a first data set stored in a first database 101 and a second data set stored in a second database 102. The second data set is a data set different from the first data set. For example, the first data set is a corpus of a first field and the second data set is a corpus of a second field. A corpus is a large-scale structured collection of texts of natural language, and includes a plurality of pieces of text data.

Figure 2:
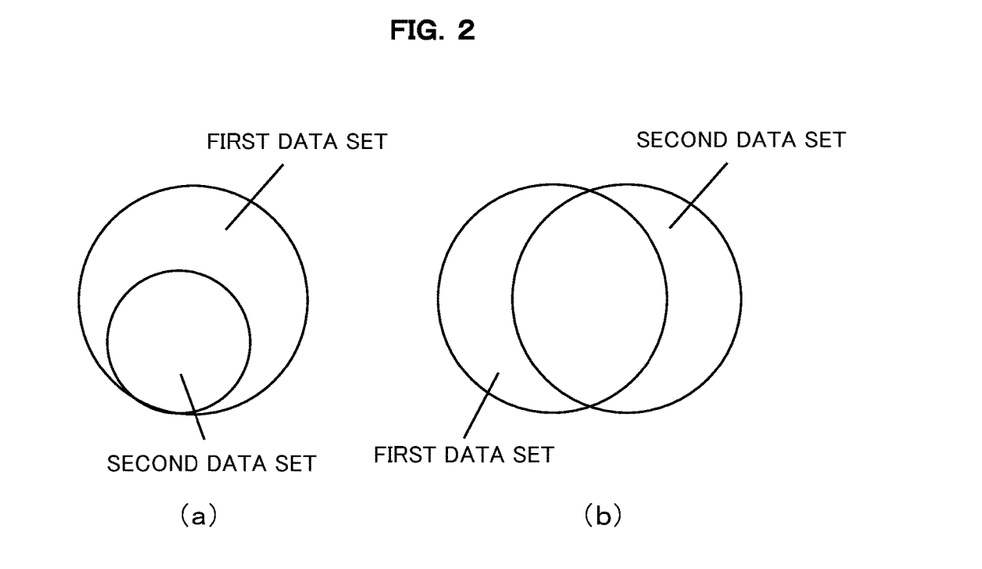
FIG. 2 is a diagram illustrating an example of a relationship between a first data set and a second data set.

FIG. 2 is a diagram schematically illustrating an example of a relationship between the first data set and the second data set. FIG. 2(a) illustrates a relationship in which the second data set is included in the first data set. For example, in this relationship, the second data set is a corpus related to a specific disease field, and the first data set is a corpus related to the entire medical field including the specific disease. FIG. 2(b) illustrates a relationship having data included only in the first data set, data included only in the second data set, and data commonly included both in the first data set and the second data set. For example, the first data set is a corpus related to a biomedical field, and the second data set is a corpus related to a field of nutritional medicine.

The first vector computation unit 1 acquires a first data set from the first database 101, and forms a first vector space by computing, from a plurality of pieces of data included in the first data set, a plurality of feature vectors related to a first predetermined item reflecting a relationship between the plurality of pieces of data and a plurality of predetermined elements included in the data. Here, when the first data set is a corpus of a first field, the first predetermined item is a word, and the first vector computation unit 1 computes a plurality of word feature vectors reflecting a relationship between a plurality of texts and a plurality of words included in the texts from a plurality of pieces of text data included in the corpus of the first field. A specific method of computing the word feature vectors will be described later.

The second vector computation unit 2 forms a second vector space by computing, from a plurality of pieces of data included in the second data set, a plurality of feature vectors reflecting a relationship between the plurality of pieces of data and a plurality of predetermined elements included in the data and related to a second predetermined item, which is the same as or different from the first predetermined item. Here, when the second data set is a corpus of a second field, the second predetermined item is also a word, and the second vector computation unit 2 computes a plurality of word feature vectors reflecting a relationship between a plurality of texts and a plurality of words included in the texts from a plurality of pieces of text data included in the corpus of the second field.

Figure 3:
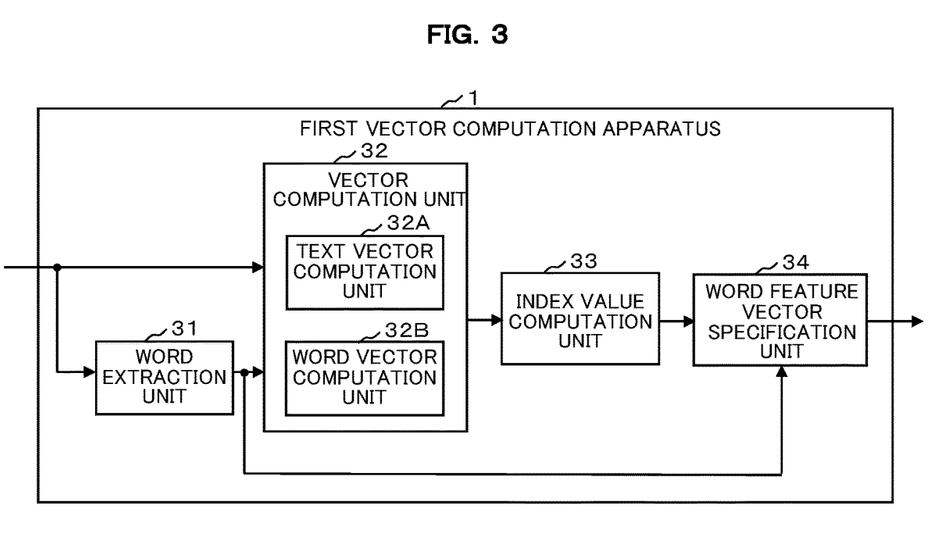
FIG. 3 is a block diagram illustrating a specific functional configuration example of a first vector computation unit.

Here, a method of computing the word feature vectors will be described. FIG. 3 is a block diagram illustrating a specific functional configuration example of the vector computation unit 1. As illustrated in FIG. 3, the vector computation unit 1 includes a word extraction unit 31, a vector computation unit 32, an index value computation unit 33, and a word feature vector specification unit 34 as specific functional configurations thereof. The vector computation unit 32 includes a text vector computation unit 32A and a word vector computation unit 32B as more specific functional configurations.

Note that the second vector computation unit 2 has a similar functional configuration as that of FIG. 3. Even though FIG. 1 illustrates a configuration including the first vector computation unit 1 and the second vector computation unit 2, the invention is not limited thereto. For example, only one of the vector computation units of the configuration illustrated in FIG. 3 may be included, and processing on the first data set and the second data set may be performed by the one vector computation unit.

The word extraction unit 31 analyzes m texts (m is an arbitrary integer of 2 or more) and extracts n words (n is an arbitrary integer of 2 or more) from the m texts. As a method of analyzing texts, for example, a known morphological analysis can be used. The word extraction unit 31 may extract morphemes of all parts of speech divided by the morphological analysis as words, or may extract only morphemes of a specific part of speech as words.

Note that the same word may be included in the m texts a plurality of times. In this case, the word extraction unit 31 does not extract the plurality of the same words, and extracts only one. That is, the n words extracted by the word extraction unit 31 refer to n types of words.

The vector computation unit 32 computes m text vectors and n word vectors from the m texts and the n words. Here, the text vector computation unit 32A converts each of the m texts to be analyzed by the word extraction unit 31 into a q-dimensional vector (q is an arbitrary integer of 2 or more) according to a predetermined rule, thereby computing the m text vectors including q axis components. In addition, the word vector computation unit 32B converts each of the n words extracted by the word extraction unit 31 into a q-dimensional vector according to a predetermined rule, thereby computing the n word vectors including q axis components.

In the present embodiment, as an example, a text vector and a word vector are computed as follows. Now, a set S=<d∈D, w∈W> including the m texts and the n words is considered. Here, a text vector $d_i\rightarrow$ and a word vector $w_j\rightarrow$ (hereinafter, the symbol "→" indicates a vector) are associated with each text $d_i$ (i=1, 2, . . . , m) and each word $w_j$ (j=1, 2, . . . , n), respectively. Then, a probability $P(w_j|d_i)$ shown in the following Equation (1) is calculated with respect to an arbitrary word $w_j$ and an arbitrary text $d_i$.

[Equation 1]

$$P(w_j|d_i) = \frac{\exp(\vec{w}_j \cdot \vec{d}_i)}{\sum_{k=1}^{n} \exp(\vec{w}_k \cdot \vec{d}_i)} \qquad (1)$$

Note that the probability $P(w_j|d_i)$ is a value that can be computed in accordance with a probability p disclosed in, a follow known document. "'Distributed Representations of Sentences and Documents' by Quoc Le and Tomas Mikolov, Google Inc; Proceedings of the 31st International Conference on Machine Learning Held in Bejing, China on 22-24 Jun. 2014" This known document states that, for example, when there are three words "the", "cat", and "sat", "on" is predicted as a fourth word, and a computation formula of the prediction probability p is described.

The probability p(wt|wt−k, . . . , wt+k) described in the known document is a correct answer probability when another word wt is predicted from a plurality of words wt−k, wt+k. Meanwhile, the probability $P(w_j|d_i)$ shown in Equation (1) used in the present embodiment represents a correct answer probability that one word $w_j$ of n words is predicted from one text $d_i$ of m texts. Predicting one word $w_j$ from one text $d_i$ means that, specifically, when a certain text $d_i$ appears, a possibility of including the word w in the text $d_i$ is predicted.

Note that since Equation (1) is symmetrical with respect to $d_i$ and $w_j$, a probability $P(d_i|w_j)$ that one text $d_i$ of m texts is predicted from one word $w_j$ of n words may be calculated. Predicting one text $d_i$ from one word $w_j$ means that, when a certain word $w_j$ appears, a possibility of including the word w in the text $d_i$ is predicted.

In Equation (1), an exponential function value is used, where e is the base and the inner product of the word vector w→ and the text vector d→ is the exponent. Then, a ratio of an exponential function value calculated from a combination of a text $d_i$ and a word $w_j$ to be predicted to the sum of n exponential function values calculated from each combination of the text $d_i$ and n words $w_k$ (k=1, 2, . . . , n) is calculated as a correct answer probability that one word $w_j$ is expected from one text $d_i$.

Here, the inner product value of the word vector $w_j$→ and the text vector $d_i$→ can be regarded as a scalar value when the word vector $w_j$→ is projected in a direction of the text vector $d_i$→, that is, a component value in the direction of the text vector $d_i$→ included in the word vector $w_j$→, which can be considered to represent a degree at which the word $w_j$ contributes to the text $d_i$. Therefore, obtaining the ratio of the exponential function value calculated for one word $W_j$ to the sum of the exponential function values calculated for n words $w_k$ (k=1, 2, . . . , n) using the exponential function value calculated using the inner product corresponds to obtaining the correct answer probability that one word $w_j$ of n words is predicted from one text $d_i$.

Note that here, a calculation example using the exponential function value using the inner product value of the word vector w→ and the text vector d→ as an exponent has been described. However, the exponential function value may not be used. Any calculation formula using the inner product value of the word vector w→ and the text vector d→ may be used. For example, the probability may be obtained from the ratio of the inner product values itself.

Next, the vector computation unit 32 computes the text vector $d_i$→ and the word vector $w_j$→ that maximize a value L of the sum of the probability $P(w_j|d_i)$ computed by Equation (1) for all the set S as shown in the following Equation (2). That is, the text vector computation unit 32A and the word vector computation unit 32B compute the probability $P(w_j|d_i)$ computed by Equation (1) for all combinations of the m texts and the n words, and compute the text vector $d_i$→ and the word vector $w_j$→ that maximize a target variable L using the sum thereof as the target variable L.

[Equation 2]

$$L=\Sigma_{d \in D}\Sigma_{w \in W} \#(w,d)p(w|d) \quad (2)$$

Maximizing the total value L of the probability $P(w_j|d_i)$ computed for all the combinations of the m texts and the n words corresponds to maximizing the correct answer probability that a certain word $w_j$ (j=1, 2, ..., n) is predicted from a certain text $d_i$ (i=1, 2, ..., m). That is, the vector computation unit 32 can be considered to compute the text vector $d_i$→ and the word vector $w_j$→ that maximize the correct answer probability.

Here, as described above, the vector computation unit 32 converts each of the m texts $d_i$ into a q-dimensional vector to compute the m texts vectors $d_i$→ including the q axis components, and converts each of the n words into a q-dimensional vector to compute the n word vectors $w_j$→ including the q axis components, which corresponds to computing the text vector $d_i$→ and the word vector $w_j$→ that maximize the target variable L by making q axis directions variable.

The index value computation unit 33 computes each of the inner products of the m text vectors $d_i$→ and the n word vectors $w_j$→ computed by the vector computation unit 32, thereby computing index values reflecting the relationship between the m texts $d_i$ and the n words $w_j$. In the present embodiment, as shown in the following Equation (3), the index value computation unit 33 obtains the product of a text matrix D having the respective q axis components ($d_{11}$ to $d_{mq}$) of the m text vectors $d_i$→ as respective elements and a word matrix W having the respective q axis components ($w_{11}$ to $w_{nq}$) of the n word vectors $w_j$→ as respective elements, thereby computing an index value matrix DW having m×n index values as elements. Here, $W^t$ is the transposed matrix of the word matrix.

[Equation 3]

$$D = \begin{pmatrix} d_{11} & d_{12} & \cdots & d_{1q} \\ d_{21} & d_{22} & \cdots & d_{2q} \\ \vdots & \vdots & \ddots & \vdots \\ d_{m1} & d_{m2} & \cdots & d_{mq} \end{pmatrix} \quad W = \begin{pmatrix} w_{11} & w_{12} & \cdots & w_{1q} \\ w_{21} & w_{22} & \cdots & w_{2q} \\ \vdots & \vdots & \ddots & \vdots \\ w_{m1} & w_{m2} & \cdots & w_{mq} \end{pmatrix} \quad DW = D * W^t = \begin{pmatrix} dw_{11} & dw_{12} & \cdots & dw_{1n} \\ dw_{21} & dw_{22} & \cdots & dw_{2n} \\ \vdots & \vdots & \ddots & \vdots \\ dw_{m1} & dw_{m2} & \cdots & dw_{mn} \end{pmatrix} \quad (3)$$

Each element of the index value matrix DW computed in this manner may indicate which word contributes to which text and to what extent and which text contributes to which word and to what extent. For example, an element $dw_{12}$ in the first row and the second column may be a value indicating a degree at which the word $w_2$ contributes to a text $d_i$ and may be a value indicating a degree at which the text $d_i$ contributes to a word $w_2$. In this way, each row of the index value matrix DW can be used to evaluate the similarity of a text, and each column can be used to evaluate the similarity of a word.

Figure 4:
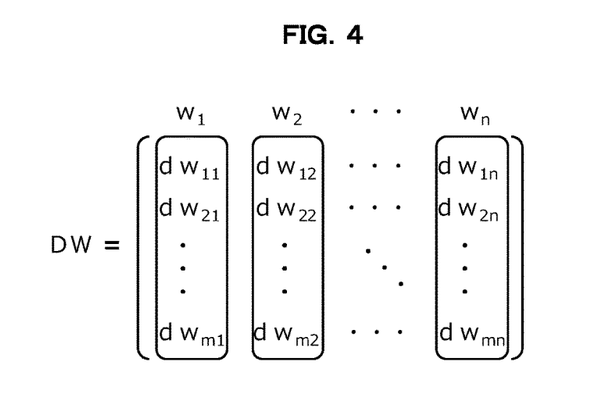
FIG. 4 is a diagram illustrating an example of a word feature vector.

In the index value matrix DW computed by the index value computation unit 33, for each of the n words, a word feature vector specification unit 34 specifies, as a word feature vector, a word index value group including index values of m texts for one word (word index value group included in one column of the index value matrix DW). That is, as illustrated in FIG. 4, the word feature vector specification unit 34 specifies a word index value group including index values of m texts included in each column of the index value matrix DW as a word feature vector for each of the n words.

The word feature vector specification unit 34 provided in the first vector computation unit 1 associates the plurality of specified word feature vectors with the words extracted by a word extraction unit 31 and stores the word feature vectors in the first feature vector storage unit 11. The first vector space is formed by the plurality of word feature vectors stored in the first feature vector storage unit 11. Further, the word feature vector specification unit 34 provided in the second vector computation unit 2 associates the plurality of specified word feature vectors with the words extracted by the word extraction unit 31 and stores the word feature vectors in the second feature vector storage unit 12. The second vector space is formed by the plurality of word feature vectors stored in the second feature vector storage unit 12.

The vector mapping unit 3 maps a feature vector included in the first vector space, which is a feature vector of an item not synonymous with a feature vector included in the second vector space (hereinafter referred to as a non-synonymous feature vector), from the first vector space to the second vector space according to a mapping vector. Note that, in the following description, a feature vector included in the first vector space, which is a feature vector of an item synonymous with a feature vector included in the second vector space is referred to as a synonymous feature vector.

When the first data set and the second data set are corpuses of the respective fields, that is, when a vector space is formed by a plurality of word feature vectors, the vector mapping unit 3 maps a word feature vector included in the first vector space, which is a word feature vector of a word not synonymous with a word feature vector included in the second vector space, from the first vector space to the second vector space according to a mapping vector. Which words are synonymous with which words may be defined in advance in a dictionary database.

For example, when a word feature vector of a word "KAZOKU (Japanese, meaning family)" is included in the first vector space, and a word feature vector of a word "FAMILY (loanword)" is included in the second vector space, since "KAZOKU" and "FAMILY" can be regarded as synonymous words, the word feature vector of "KAZOKU" included in the first vector space is excluded from mapping. On the other hand, when a word feature vector of a word "HAHA (Japanese, meaning mother)" is included in the first vector space, and any word feature vector of a word "HAHA", "MOTHER (loanword)", or a synonym thereof is not included in the second vector space, the word feature vector of "HAHA" included in the first vector space is subjected to mapping.

A mapping vector used for mapping is, for example, a matrix including eigenvectors computed from synonymous feature vectors commonly included in both the first vector space and the second vector space among a plurality of feature vectors computed by the first vector computation unit 1 and a plurality of feature vectors computed by the second vector computation unit 2. In the above example, the word feature vector of "KAZOKU" included in the first vector space and the word feature vector of "FAMILY" included in the second vector space are used when computing the eigenvectors. On the other hand, the word feature vector of "HAHA" included in the first vector space is not used when computing the eigenvectors.

The eigenvectors can be computed, for example, as follows. That is, for a synonymous feature vector commonly included in both the first vector space and the second vector space as a target, the vector mapping unit 3 obtains the mapping vector by multiplying the synonymous feature vector included in the first vector space by the synonymous feature vector included in the second vector space, and multiplying left and right singular matrices obtained by singular value decomposition (SVD) of a matrix obtained by the multiplication.

Here, when the mapping vector is denoted by TV, the synonymous feature vectors included in the first vector space are denoted by $X=\{X_1, X_2, \ldots, X_k\}$ (k being the number of feature vectors used to compute the eigenvectors), the synonymous feature vectors included in the second vector space are denoted by $Y=\{Y_1, Y_2, \ldots, Y_k\}$, a left singular matrix is denoted by U, and a right singular matrix is denoted by V, the mapping vector W* is represented by the following (Equation 4). A superscript T indicates a transposed matrix.

$$W^*=U \cdot V^T (U \text{ and } V \text{ are left and right singular matrices of } SVD(Y \cdot X^T))$$ (Equation 4)

That is, the vector mapping unit 3 multiplies (a transposed vector $X^T$ of) the synonymous feature vectors X included in the first vector space by the synonymous feature vectors Y included in the second vector space, and decomposes a resultant matrix $(Y \cdot X^T)$ into three matrices U, S, and V. The matrix U is a left singular matrix, in which each column is an eigenvector of $(Y \cdot X^T)*(Y \cdot X^T)^T$. The matrix S is a square matrix, in which diagonal matrix elements indicate singular values of the matrix $(Y \cdot X^T)$, and all other values are zero. The matrix V is a right singular matrix, in which each row is an eigenvector of $(Y \cdot X^T)^T*(Y \cdot X^T)$. The vector mapping unit 3 obtains the mapping vector W* by multiplying the left singular matrix U by (the transposed matrix $V^T$ of) the right singular matrix V among the three matrices decomposed as described above.

The vector mapping unit 3 additionally stores the feature vectors mapped from the first vector space to the second vector space in the second feature vector storage unit 12. In this way, the second feature vector storage unit 12 stores the feature vectors computed by the second vector computation unit 2 and the feature vectors mapped by the vector mapping unit 3. That is, the second vector space is updated by the feature vectors mapped from the first vector space by the vector mapping unit 3.

Figure 5:
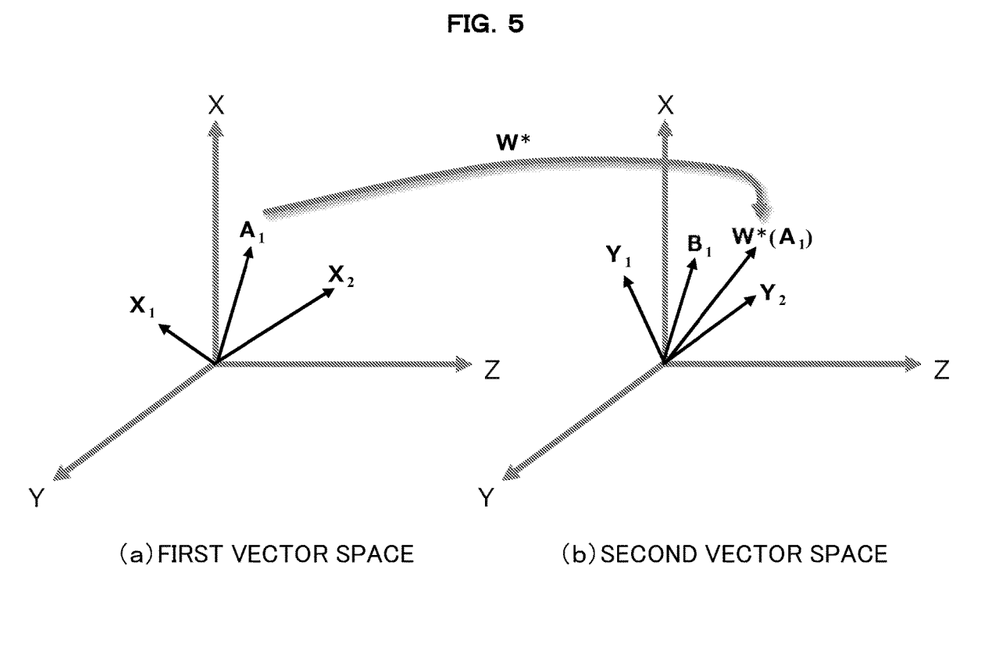
FIG. 5 is a diagram schematically illustrating processing content of a vector mapping unit.

FIG. 5 is a diagram schematically illustrating processing content of the vector mapping unit 3. Here, the number of dimensions of the feature vectors is set to "3" to indicate a three-dimensional (3D) vector space. However, the number of dimensions of the feature vectors may be "2" or larger than "3". FIG. 5(a) is the first vector space, in which $X_1$ and $X_2$ are synonymous feature vectors included in the first vector space (feature vectors synonymous with $Y_1$ and $Y_2$ included in the second vector space), and $A_1$ is a non-synonymous feature vector included in the first vector space (a feature vector having no synonymous feature vector in the second vector space).

FIG. 5(b) is the second vector space, in which $Y_1$ and $Y_2$ are synonymous feature vectors included in the second vector space (feature vectors synonymous with $X_1$ and $X_2$ included in the first vector space), and $B_1$ is a non-synonymous feature vector included in the second vector space (a feature vector having no synonymous feature vector in the first vector space). In addition, W* ($A_1$) is a feature vector obtained by mapping the non-synonymous feature vector $A_1$ included in the first vector space to the second vector space by the mapping vector W. The mapping vector W* in this case is a matrix of eigenvectors computed by the above (Equation 4) for the synonymous feature vectors $X_1, X_2, Y_1$, and $Y_2$ commonly included in both the first vector space and the second vector space as targets.

An eigenvector computed based on the synonymous feature vectors $X_1, X_2, Y_1$, and $Y_2$ common to both the first vector space and the second vector space is a vector reflecting features common to both the vector spaces. Therefore, by using this eigenvector as the mapping vector W*, the feature vector $A_1$ included in the first vector space is mapped to an appropriate position in the second vector space. Mapping to an appropriate position means that the feature vector $A_1$ is mapped to the feature vector W*($A_1$) so that a relationship between the feature vector $A_1$ in the first vector space and the feature vector W*($A_1$) obtained by mapping the feature vector $A_1$ to the second vector space becomes a relationship roughly imitating a relationship between the feature vector $X_1$ and the feature vector $Y_1$ synonymous therewith and a relationship between the feature vector $X_2$ and the feature vector $Y_2$ synonymous therewith.

The data analyzing unit 4 performs data analysis on, as targets, a plurality of feature vectors computed in the second vector space by the second vector computation unit 2 and a feature vector mapped from the first vector space to the second vector space by the vector mapping unit 3 in the updated second vector space. Content of data analysis is any content. For example, it is possible to analyze a relationship between feature vectors by computing a degree of similarity between feature vectors included in the second vector space. For example, it is also possible to perform data analysis described in PTL 1.

In the example of FIG. 5, in the second vector space updated as illustrated in FIG. 5(b), the data analyzing unit 4 can perform data analysis on the feature vector including the feature vector W*($A_1$) mapped from the first vector space in addition to the feature vectors $Y_1, Y_2$, and $B_1$ originally present in the second vector space. In this way, it is possible to analyze not only a degree of similarity between the feature vectors $Y_1, Y_2$, and $B_1$, but also a degree of similarity between the feature vectors $Y_1, Y_2$, and $B_1$ and the feature vector W*($A_1$).

Here, since the feature vectors $Y_1, Y_2$, and $B_1$ are used without change, the second vector space updated by the feature vector W*($A_1$) reflects features of the original second vector space formed based on the second data set without change. In addition, data analysis can be performed on, as a target, also the feature vector W*($A_1$) complemented in the form of mapping from the first vector space to the second vector space. For example, when feature vectors are word feature vectors, it is possible to analyze a relationship between words including a word extracted only from the first data set in addition to a word extracted from the second data set based on a degree of similarity between the feature vectors. In the case of the example illustrated in FIG. 5 (b), it is possible to obtain new knowledge that words corresponding to the feature vector W*($A_1$) mapped from the first vector space have a close relationship with words corresponding to the feature vectors $Y_2$ and $B_1$.

Note that, in the above embodiment, a description has been given of an example in which both the first data set and the second data set are corpora (sets of text data), and a word feature vector is computed. However, the invention is not limited thereto. Any data set can be used as long as it is possible to compute a plurality of feature vectors related to a predetermined item reflecting a relationship between a plurality of pieces of data included therein and a plurality of predetermined elements included in the data, and a data set other than text data can be used.

For example, one of the first data set and the second data set may be set to a data set of text data including a word of a compound (including a molecule or gene, the same applies hereinafter), and the other one may be set to a data set of chemical formula data in which a chemical structure of a compound is represented by a character string. As the chemical formula data, for example, it is possible to use data representing a chemical structure of a molecule in SMILES notation. SMILES notation is a method in which atoms in a compound are regarded as nodes and bonds between atoms are regarded as edges, and a chemical structure is represented by a one-line character string (alphanumeric characters in ASCII code). For example, the molecule aflatoxin $B_1$ is represented in SMILES notation as "O1C=C[C@H]([C@H]1O2)c3c2cc(OC)c4c3OC(=O)C5=C4CCC(=O)5". The word of the molecule aflatoxin $B_1$ is synonymous with a chemical formula in which the molecule is represented in SMILES notation.

Figure 6:
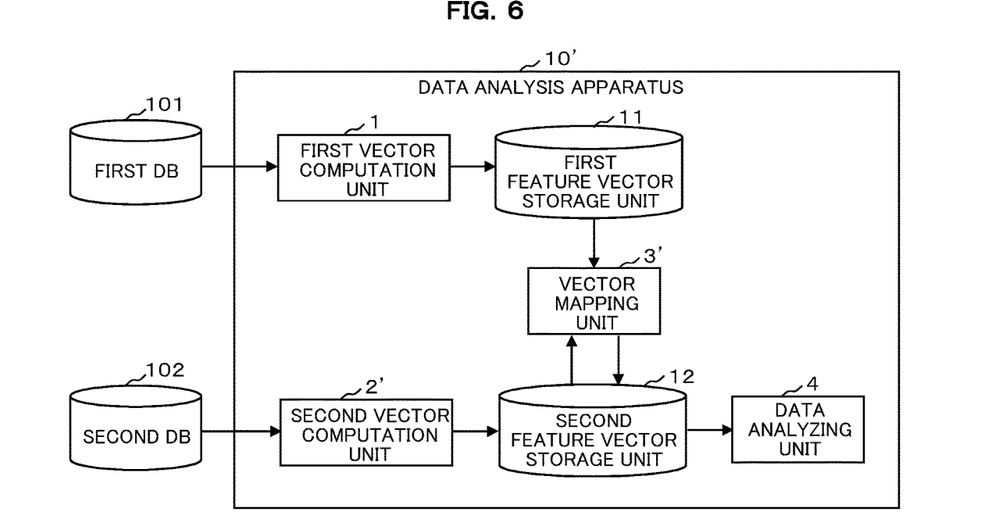
FIG. 6 is a block diagram illustrating another functional configuration example of the data analysis apparatus according to the present embodiment.

Hereinafter, a description will be given of the case where the first data set is set to a data set of text data, and the second data set is set to a data set of chemical formula data. FIG. 6 is a block diagram illustrating a functional configuration example of a data analysis apparatus 10' in this case. In FIG. 6, ones denoted by the same reference numerals as those illustrated in FIG. 1 have the same functions, and thus duplicate descriptions are omitted here. The data analysis apparatus 10' illustrated in FIG. 6 includes a second vector computation unit 2' and a vector mapping unit 3' in place of the second vector computation unit 2 and the vector mapping unit 3 illustrated in FIG. 1.

In the configuration illustrated in FIG. 6, the first vector computation unit 1 computes a plurality of word feature vectors reflecting a relationship between a plurality of texts and a plurality of words included in the texts from a plurality of pieces of text data included in the first data set. The word feature vector specification unit 34 provided in the first vector computation unit 1 associates a plurality of specified word feature vectors with words extracted by the word extraction unit 31, and stores the word feature vectors in the first feature vector storage unit 11. The first vector space is formed by the plurality of word feature vectors stored in the first feature vector storage unit 11. Specific processing content thereof has been described with reference to FIG. 3.

The second vector computation unit 2' computes a plurality of chemical formula feature vectors reflecting a relationship between a plurality of chemical formulae and a plurality of character strings included in the chemical formulae from a plurality of pieces of chemical formula data included in the second data set. Here, the plurality of character strings included in the chemical formulae are a minimum unit of a group of character strings having a meaning from a viewpoint of nodes and edges in SMILES notation (corresponding to morphemes in natural language). For example, SMILES notation "O1C=C[C@H]([C@H]1O2)c3c2cc(OC)c4c3OC(=O)C5=C4CCC(=O)5" for the molecule aflatoxin $B_1$ can be decomposed into elements as follows.

O,1,C=C,[C@H],([C@H]1O2),c3,c2,cc,(OC),c4,c3,OC, (=O),C5=C4,CCC,(=O),5

Figure 7:
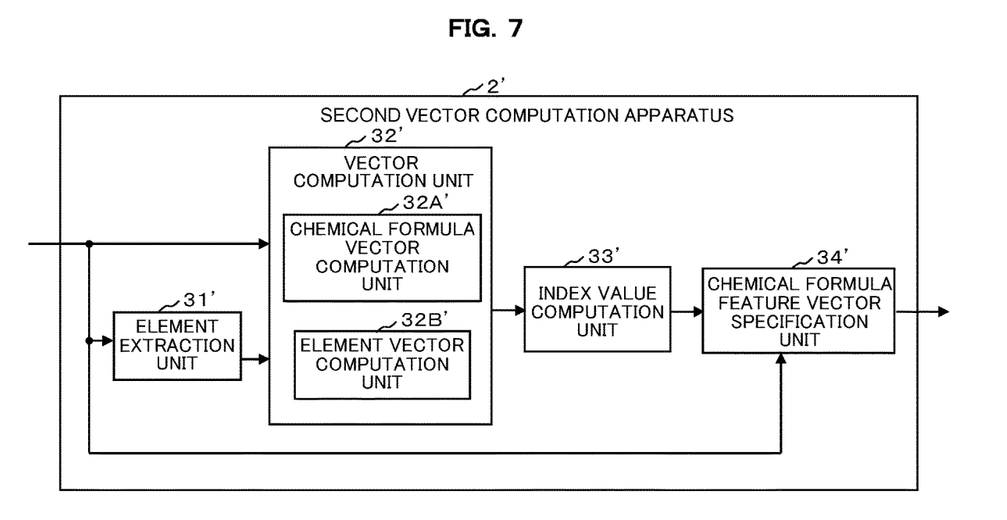
FIG. 7 is a block diagram illustrating another functional configuration example of a second vector computation unit.

Specific processing content of the second vector computation unit 2' will be described based on FIG. 7. As illustrated in FIG. 7, the second vector computation unit 2' includes an element extraction unit 31', a vector computation unit 32', an index value computation unit 33', and a chemical formula feature vector specification unit 34' in place of the word extraction unit 31, a vector computation unit 32, the index value computation unit 33, and the word feature vector specification unit 34 illustrated in FIG. 3. The vector computation unit 32' includes a chemical formula vector computation unit 32A' and an element vector computation unit 32B' in place of a text vector computation unit 32A and a word vector computation unit 32B.

The element extraction unit 31' analyzes i chemical formulae, and extracts j elements (minimum unit of a group of character strings having a meaning from a viewpoint of nodes and edges) from the i chemical formulae.

The vector computation unit 32' computes i chemical formula vectors C→ and j element vectors from the i chemical formulae and the j elements. Here, the chemical formula vector computation unit 32A' converts each of the i chemical formulae analyzed by the element extraction unit 31' into a q-dimensional vector according to a predetermined rule, thereby computing the i chemical formula vectors C including q axis components. In addition, the element vector computation unit 32B' converts each of the j elements extracted by the element extraction unit 31' into a q-dimensional vector according to a predetermined rule, thereby computing the j element vectors F→ including q axis components.

The index value computation unit 33' computes each inner product of the i chemical formula vectors C→ and the j element vectors F→ computed by the vector computation unit 32', thereby computing an index value matrix CF reflecting a relationship between the i chemical formulae and the j elements.

Figure 8:
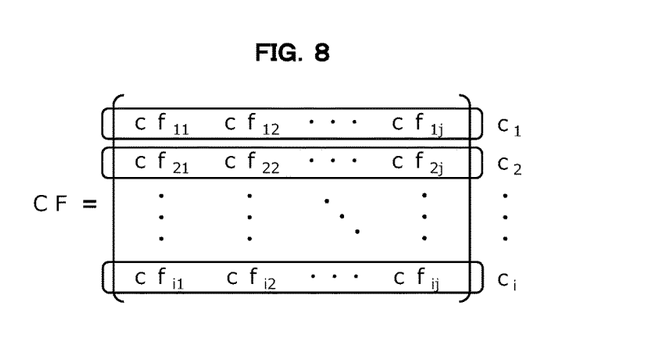
FIG. 8 is a diagram illustrating an example of a chemical formula feature vector.

In the index value matrix CF computed by the index value computation unit 33', for each of the i chemical formulae, the chemical formula feature vector specification unit 34' specifies, as a chemical formula feature vector, a chemical formula index value group including index values of the j elements for one chemical formal (a chemical formula index value group included in one row of the index value matrix CF). That is, as illustrated in FIG. 8, the chemical formula feature vector specification unit 34' specifies a chemical formula index value group including index values of the j elements included in each row of the index value matrix CF as a chemical formula feature vector for each of the i chemical formulae.

The chemical formula feature vector specification unit 34' associates the plurality of specified chemical formula feature vectors with a chemical formal indicated by chemical formula data input to the second vector computation unit 2', and stores the specified chemical formula feature vectors in the second feature vector storage unit 12. The second vector space is formed by the plurality of chemical formula feature vectors stored in the second feature vector storage unit 12.

The vector mapping unit 3' of FIG. 6 maps a word feature vector included in the first vector space, which is a word feature vector of a word not synonymous with a chemical formula of a chemical formula feature vector included in the second vector space, from the first vector space to the second vector space according to the mapping vector W. The vector mapping unit 3' additionally stores the word feature vector mapped from the first vector space to the second vector space in the second feature vector storage unit 12. When such mapping is performed, the second vector space formed by the plurality of chemical formula feature vectors is complemented by a word feature vector of a word not synonymous with a chemical formula of a chemical formula feature vector belonging to the second vector space from the first vector space.

Note that the case where the first data set is set to a data set of text data, and the second data set is set to a data set of chemical formula data has been described here. However, conversely, the first data set may be set to a data set of chemical formula data, and the second data set may be set to a data set of text data. In this case, instead of the first vector computation unit 1 illustrated in FIG. 1, a first vector computation unit 1' is provided, and the first vector computation unit 1' computes a chemical formula feature vector, while the second vector computation unit 2 computes a word feature vector.

In addition, the vector mapping unit 3' maps a chemical formula feature vector included in the first vector space, which is a chemical formula feature vector of a chemical formula not synonymous with a word of a word feature vector included in the second vector space, from the first vector space to the second vector space according to the mapping vector. When such mapping is performed, the second vector space formed by the plurality of word feature vectors is complemented by a chemical formula feature vector of a compound not synonymous with a word of a word feature vector belonging to the second vector space from the first vector space.

As described in detail above, in the present embodiment, the first vector space is formed by computing a plurality of feature vectors from a plurality of pieces of data included in the first data set, and the second vector space is formed by computing a plurality of feature vectors from a plurality of pieces of data included in the second data set. In addition, a feature vector included in the first vector space, which is a feature vector of an item not synonymous with a feature vector included in the second vector space, is mapped from the first vector space to the second vector space according to a mapping vector. Then, in the second vector space, data analysis is performed on, as targets, a plurality of feature vectors computed in the second vector space and feature vectors mapped from the first vector space to the second vector space.

According to the present embodiment configured as described above, a first vector space and a second vector space are formed by individually computing a plurality of feature vectors from each of a plurality of pieces of data included in a first data set and a plurality of pieces of data included in a second data set, and thus the first vector space and the second vector space utilize the features of the first data set and the second data set, respectively, without change. In addition, while leaving the plurality of feature vectors included in the second vector space without change, by mapping feature vectors of items not synonymous with the feature vectors from the first vector space to the second vector space, feature vectors derived from the first vector space are added to the second vector space. Then, data analysis is performed on, as targets, the feature vectors originally included in the second vector space and the feature vectors added by mapping from the first vector space. In this way, according to the present embodiment, it is possible to perform data analysis extending coverage to a data set wider than the second data set while fully utilizing the features of the original second vector space formed from the second data set.

Note that, in the above embodiment, a description has been given of an example in which an index value matrix is computed, and a word feature vector or a chemical formula feature vector is specified from the index value matrix. However, the invention is not limited thereto. For example, a word vector computed by the word vector computation unit 32B may be used as a word feature vector. In addition, a chemical formula vector computed by the chemical formula vector computation unit 32A' may be used as a chemical formula feature vector. In addition, the method of computing feature vectors described in the above embodiment is an example, and the invention is not limited thereto.

Further, in the above embodiment, a description has been given of an example in which eigenvectors computed from synonymous feature vectors commonly included in both the first vector space and the second vector space are used as mapping vectors, and the eigenvectors are computed by (Equation 4). However, (Equation 4) is an example, and the invention is not limited thereto. The present embodiment is significant in that the mapping vectors are computed based on synonymous feature vectors extracted from both the first vector space and the second vector space. Any vector computed to satisfy this requirement can be used as a mapping vector of the present embodiment. For example, the eigenvector described in the above embodiment is an index representing a feature of linear transformation. However, a mapping vector that performs other linear transformation or nonlinear transformation may be used.

Typical examples of nonlinear transformation may include a deep learning model constructed by combining neural networks. In this case, a nonlinear mapping model can be constructed by using a feature vector X of a first vector space and a feature vector Y of a second vector space synonymous with each other, and by training the model in manner that inputting the feature vector X to the deep learning model and outputting the feature vector Y from the deep learning model.

In addition, the above-described embodiment is merely an example of specific implementation of the invention, and the technical scope of the invention should not be construed in a limited manner. Thus, the invention can be implemented in various forms without departing from spirit or essential characteristics thereof.

REFERENCE SIGNS LIST

1: first vector computation unit
2, 2': second vector computation unit
3, 3': vector mapping unit
4: data analyzing unit
10, 10': data analysis apparatus
31: word extraction unit
31': element extraction unit
32, 32': vector computation unit
32A: text vector computation unit
32A': chemical formula vector computation unit
32B: word vector computation unit
32B': element vector computation unit
33, 33': index value computation unit
34: word feature vector specification unit
34': chemical formula feature vector specification unit

The invention claimed is:

1. A data analysis apparatus comprising:
a first vector computation unit configured to form a first vector space in a first feature vector storage unit by computing, from a plurality of pieces of data included in a first data set stored in a first database, a plurality of feature vectors related to a first predetermined item reflecting a relationship between the plurality of pieces of data and a plurality of predetermined elements included in the data and storing the computed plurality of feature vectors in the first feature vector storage unit;
a second vector computation unit configured to form a second vector space in a second feature vector storage unit by computing, from a plurality of pieces of data included in a second data set stored in a second database and different from the first data set, a plurality of feature vectors reflecting a relationship between the plurality of pieces of data and a plurality of predetermined elements included in the data, the plurality of feature vectors being related to the same or a different second predetermined item as or from the first predetermined item and storing the computed plurality of feature vectors in the second feature vector storage unit;
a vector mapping unit configured to map a feature vector included in the first vector space, which is a feature vector of an item not synonymous with a feature vector included in the second vector space, from the first vector space to the second vector space according to a mapping vector and update the second vector space by additionally storing the mapped feature vector to the second feature vector storage unit; and
a data analyzing unit configured to perform data analysis on, as targets, a plurality of feature vectors stored in the second feature vector storage unit by the second vector computation unit and a feature vector additionally stored in the second feature vector storage unit by the vector mapping unit in the updated second vector space.

2. The data analysis apparatus according to claim 1, wherein the mapping vector is an eigenvector computed from a synonymous feature vector commonly included in both the first vector space and the second vector space among the plurality of feature vectors computed by the first vector computation unit and the plurality of feature vectors computed by the second vector computation unit.

3. The data analysis apparatus according to claim 2, wherein, for the synonymous feature vector commonly included in both the first vector space and the second vector space as a target, the vector mapping unit obtains the eigenvector by multiplying the synonymous feature vector included in the first vector space by the synonymous feature vector included in the second vector space, and multiplying left and right singular matrices obtained by singular value decomposition of a matrix obtained by the multiplication.

4. The data analysis apparatus according to claim 3, wherein:
the first data set is a corpus of a first field, the first predetermined item is a word, and the first vector computation unit computes a plurality of word feature vectors reflecting a relationship between a plurality of texts and a plurality of words included in the texts from a plurality of pieces of text data included in the corpus of the first field,
the second data set is a corpus of a second field, the second predetermined item is a word, and the second vector computation unit computes a plurality of word feature vectors reflecting a relationship between a plurality of texts and a plurality of words included in the texts from a plurality of pieces of text data included in the corpus of the second field, and
the vector mapping unit maps a word feature vector included in the first vector space, which is a word feature vector of a word not synonymous with a word feature vector included in the second vector space, from the first vector space to the second vector space according to the mapping vector.

5. The data analysis apparatus according to claim 3, wherein:
any one of the first data set and the second data set is a data set of text data including a word of a compound, and the other one is a data set of chemical formula data representing a chemical structure of a compound as a character string,
any one of the first vector computation unit and the second vector computation unit computes a plurality of word feature vectors reflecting a relationship between a plurality of texts and a plurality of words included in the texts from a plurality of pieces of text data,
the other one of the first vector computation unit and the second vector computation unit computes a plurality of chemical formula feature vectors reflecting a relationship between a plurality of chemical formulae and a plurality of character strings included in the chemical formulae from a plurality of pieces of chemical formula data, and
the vector mapping unit maps a word feature vector included in the first vector space, which is a word feature vector of a word not synonymous with a chemical formula of a chemical formula feature vector included in the second vector space, from the first vector space to the second vector space according to the mapping vector, or maps a chemical formula feature vector included in the first vector space, which is a chemical formula feature vector of a chemical formula not synonymous with a word of a word feature vector included in the second vector space, from the first vector space to the second vector space according to the mapping vector.

6. The data analysis apparatus according to claim 2, wherein:
the first data set is a corpus of a first field, the first predetermined item is a word, and the first vector computation unit computes a plurality of word feature vectors reflecting a relationship between a plurality of texts and a plurality of words included in the texts from a plurality of pieces of text data included in the corpus of the first field,
the second data set is a corpus of a second field, the second predetermined item is a word, and the second vector computation unit computes a plurality of word feature vectors reflecting a relationship between a plurality of texts and a plurality of words included in the texts from a plurality of pieces of text data included in the corpus of the second field, and
the vector mapping unit maps a word feature vector included in the first vector space, which is a word feature vector of a word not synonymous with a word feature vector included in the second vector space, from the first vector space to the second vector space according to the mapping vector.

7. The data analysis apparatus according to claim 2, wherein:

any one of the first data set and the second data set is a
data set of text data including a word of a compound,
and the other one is a data set of chemical formula data
representing a chemical structure of a compound as a
character string, any one of the first vector computation unit and the second
vector computation unit computes a plurality of word
feature vectors reflecting a relationship between a plurality of texts and a plurality of words included in the
texts from a plurality of pieces of text data, the other one of the first vector computation unit and the
second vector computation unit computes a plurality of
chemical formula feature vectors reflecting a relationship between a plurality of chemical formulae and a
plurality of character strings included in the chemical
formulae from a plurality of pieces of chemical formula
data, and the vector mapping unit maps a word feature vector
included in the first vector space, which is a word
feature vector of a word not synonymous with a chemical formula of a chemical formula feature vector
included in the second vector space, from the first
vector space to the second vector space according to the
mapping vector, or maps a chemical formula feature
vector included in the first vector space, which is a
chemical formula feature vector of a chemical formula
not synonymous with a word of a word feature vector
included in the second vector space, from the first
vector space to the second vector space according to the
mapping vector.

8. The data analysis apparatus according to claim 1,
wherein:

the first data set is a corpus of a first field, the first
predetermined item is a word, and the first vector
computation unit computes a plurality of word feature
vectors reflecting a relationship between a plurality of
texts and a plurality of words included in the texts from
a plurality of pieces of text data included in the corpus
of the first field, the second data set is a corpus of a second field, the
second predetermined item is a word, and the second
vector computation unit computes a plurality of word
feature vectors reflecting a relationship between a plurality of texts and a plurality of words included in the
texts from a plurality of pieces of text data included in
the corpus of the second field, and the vector mapping unit maps a word feature vector
included in the first vector space, which is a word
feature vector of a word not synonymous with a word
feature vector included in the second vector space, from
the first vector space to the second vector space according to the mapping vector.

9. The data analysis apparatus according to claim 8,
wherein each of the first vector computation unit and second
vector computation unit comprises:

a word extraction unit that analyzes m texts, wherein m is
an arbitrary integer of 2 or more, shown by text data,
and extracts n words, wherein n is an arbitrary integer
of 2 or more, from the m texts;

a text vector computation unit that converts each of the m
texts into a q-dimensional vector, wherein q is an
arbitrary integer larger than 2, according to a predetermined rule, thereby computing m text vectors including
q axis components;

a word vector computation unit that converts each of the
n words into a q-dimensional vector according to a
predetermined rule, thereby computing n word vectors
including q axis components;

an index value computation unit that obtains each of the
inner products of the m text vectors and the n word
vectors, thereby computing m×n index values reflecting
a relationship between the m texts and the n words;

and a word feature vector specification unit that specifies,
as the word feature vector, a word index value group
including index values of m texts for one word for each
of the n words.

10. The data analysis apparatus according to claim 1,
wherein:

any one of the first data set and the second data set is a
data set of text data including a word of a compound,
and the other one is a data set of chemical formula data
representing a chemical structure of a compound as a
character string, any one of the first vector computation unit and the second
vector computation unit computes a plurality of word
feature vectors reflecting a relationship between a plurality of texts and a plurality of words included in the
texts from a plurality of pieces of text data, the other one of the first vector computation unit and the
second vector computation unit computes a plurality of
chemical formula feature vectors reflecting a relationship between a plurality of chemical formulae and a
plurality of character strings included in the chemical
formulae from a plurality of pieces of chemical formula
data, and the vector mapping unit maps a word feature vector
included in the first vector space, which is a word
feature vector of a word not synonymous with a chemical formula of a chemical formula feature vector
included in the second vector space, from the first
vector space to the second vector space according to the
mapping vector, or maps a chemical formula feature
vector included in the first vector space, which is a
chemical formula feature vector of a chemical formula
not synonymous with a word of a word feature vector
included in the second vector space, from the first
vector space to the second vector space according to the
mapping vector.

11. The data analysis apparatus according to claim 10,
wherein any one of the first vector computation units and
second vector computation unit comprises:

a word extraction unit that analyzes m texts, wherein m is
an arbitrary integer of 2 or more, shown by text data,
and extracts n words, wherein n is an arbitrary integer
of 2 or more, from the m texts;

a text vector computation unit that converts each of the m
texts into a q-dimensional vector, wherein q is an
arbitrary integer larger than 2, according to a predetermined rule, thereby computing m text vectors including
q axis components;

a word vector computation unit that converts each of the
n words into a q-dimensional vector according to a
predetermined rule, thereby computing n word vectors
including q axis components;

an index value computation unit that obtains each of inner
products of the m text vectors and the n word vectors,
thereby computing m×n index values reflecting a relationship between the m texts and the n words, and a word feature vector specification unit that specifies, as
the word feature vector, a word index value group
including index values of m texts for one word for each
of the n words, and the other of the first vector computation unit and second vector computation unit comprising:

an element extraction unit that analyzes i chemical formulae, wherein i is an arbitrary integer of 2 or more, and extracts j elements, wherein j is an arbitrary integer of 2 or more, which are the minimum unit of a group of character strings having meaning from the i chemical formulae;

a chemical formula vector computation unit that converts each of the i chemical formulae into a q-dimensional vector according to a predetermined rule, thereby computing I chemical formula vectors including q axis components;

an element vector computation unit that converts each of the j elements into a q-dimensional vector according to a predetermined rule, thereby computing j element vectors including q axis components;

an index value computation unit that obtains each of inner products of the i chemical formula vectors and the j element vectors, thereby computing m×n index values reflecting a relationship between the i chemical formulae and the j elements;

and a chemical formula feature vector specification unit that specifies, as the chemical formula feature vector, a chemical formula index value group including index values of j elements for one chemical formula for each of the i chemical formulae.

12. A data analysis program stored on a non-transitory computer readable medium for causing a computer to function as:

a first vector computation means configured to form a first vector space in a first feature vector storage unit by computing, from a plurality of pieces of data included in a first data set stored in a first database, a plurality of feature vectors related to a first predetermined item reflecting a relationship between the plurality of pieces of data and a plurality of predetermined elements included in the data and storing the computed plurality of feature vectors in the first feature vector storage unit;

a second vector computation means configured to form a second vector space in a second feature vector storage unit by computing, from a plurality of pieces of data included in a second data set stored in a second database and different from the first data set, a plurality of feature vectors reflecting a relationship between the plurality of pieces of data and a plurality of predetermined elements included in the data, the plurality of feature vectors being related to the same or a different second predetermined item as or from the first predetermined item and storing the computed plurality of feature vectors in the second feature vector storage unit;

a vector mapping means configured to map a feature vector included in the first vector space, which is a feature vector of an item not synonymous with a feature vector included in the second vector space, from the first vector space to the second vector space according to a mapping vector and update the second vector space by additionally storing the mapped feature vector to the second feature vector storage unit; and a data analysis means configured to perform data analysis on, as targets, a plurality of feature vectors stored in the second feature vector storage unit by the second vector computation means and a feature vector additionally stored in the second feature vector storage unit by the vector mapping means in the updated second vector space.

* * * * *